(12) United States Patent
Sekoguchi et al.

(10) Patent No.: US 7,120,006 B2
(45) Date of Patent: Oct. 10, 2006

(54) ION GENERATOR AND AIR CONDITIONING APPARATUS

(75) Inventors: Yoshinori Sekoguchi, Kitakatsuragi-gun (JP); Kenji Furuhashi, Hirakata (JP); Mamoru Morikawa, Yamatokooriyama (JP)

(73) Assignee: Sharp Kabushiki Kaisha, Osaka (JP)

( * ) Notice: Subject to any disclaimer, the term of this patent is extended or adjusted under 35 U.S.C. 154(b) by 81 days.

(21) Appl. No.: 10/475,121

(22) PCT Filed: Apr. 19, 2002

(86) PCT No.: PCT/JP02/03969

§ 371 (c)(1),
(2), (4) Date: Jan. 20, 2004

(87) PCT Pub. No.: WO02/087034

PCT Pub. Date: Oct. 31, 2002

(65) Prior Publication Data

US 2004/0130271 A1    Jul. 8, 2004

(30) Foreign Application Priority Data

Apr. 20, 2001 (JP) .............................. 2001-123230

(51) Int. Cl.
    *H01T 23/00* (2006.01)
(52) U.S. Cl. .................... 361/230; 361/231; 361/233
(58) Field of Classification Search ............. 361/231, 361/230, 232, 233, 229; 315/111.21, 111.01
    See application file for complete search history.

(56) References Cited

U.S. PATENT DOCUMENTS 4,210,949 A    7/1980 Masuda
4,920,266 A *  4/1990 Reale ........................ 250/324
5,047,892 A *  9/1991 Sakata et al. ............... 361/231
5,332,425 A *  7/1994 Huang ......................... 96/26
5,895,632 A *  4/1999 Nomura et al. ......... 422/186.04
6,256,825 B1 * 7/2001 Hwang ........................ 15/1.51
6,259,591 B1 * 7/2001 Pitel et al. .................. 361/212

FOREIGN PATENT DOCUMENTS

| DE | 2 412 693 A | 10/1974 |
| JP | 49-129493 A | 12/1974 |
| JP | 54-40369 A | 3/1979 |
| JP | 1-221166 A | 9/1989 |
| JP | 4-90428 A | 3/1992 |
| JP | 4-306596 A | 10/1992 |
| JP | 5-95681 A | 4/1993 |
| JP | 6-245528 A | 9/1994 |

(Continued)

*Primary Examiner*—Tuyet Thi Vo
(74) *Attorney, Agent, or Firm*—Birch Stewart Kolasch & Birch, LLP

(57) ABSTRACT

A switching transformer applies an alternating high voltage across an internal electrode and an external electrode which face each other with a glass tube as a dielectric body between them. The anode side of a diode is connected to the external electrode which is not a voltage supply side electrode, while the cathode side is grounded. When a relay connected to both the terminals of the diode is turned on, substantially equal amounts of positive ions and negative ions are generated, and a bacteria removal/disinfection effect can be obtained by emitting these positive ions and negative ions into the air. When the relay is turned off, a relatively small amount of positive ions and a relatively large amount of negative ions are generated, and a relaxation effect given by negative ions can be obtained by emitting these positive ions and negative ions into the air.

18 Claims, 13 Drawing Sheets

FOREIGN PATENT DOCUMENTS

| | | |
|---|---|---|
| JP | 7-108147 A | 4/1995 |
| JP | 08-217412 A | 8/1996 |
| JP | 8-255669 A | 10/1996 |
| JP | 10-12395 A | 1/1998 |
| JP | 11-251035 A | 9/1999 |
| JP | 2000-058290 A | 2/2000 |
| JP | 2000-167435 A | 6/2000 |
| JP | 2000-185099 A | 7/2000 |
| JP | 2001-42598 A | 2/2001 |
| JP | 2001-70830 A | 3/2001 |
| JP | 2001-179131 A | 7/2001 |
| JP | 2002-25748 A | 1/2002 |
| JP | 2002-95731 A | 4/2002 |
| JP | 2002-305070 A | 10/2002 |

* cited by examiner

ION GENERATOR AND AIR CONDITIONING APPARATUS

CROSS REFERENCE TO RELATED APPLICATIONS

This application is the national phase under 35 U.S.C. §371 of PCT International Application No. PCT/JP02/03969 which has an International filing date of Apr. 19, 2002, which designated the United States of America.

BACKGROUND OF THE INVENTION

TECHNICAL FIELD

The present invention relates to ion generators that generate ions into the air, and air conditioning apparatuses incorporating such an ion generator. Note that the air conditioning apparatus refers to a whole range of apparatuses that create any desired atmosphere by changing the physical properties of air, and examples of such apparatuses include air conditioners, air purifiers, dehumidifiers, humidifiers, and fan heaters. Refrigerators also belong to the field of air conditioning apparatuses within the scope of the present invention.

BACKGROUND ART

The air inside a room is polluted by various substances such as dust, cigarette smoke, and carbon dioxide discharged with breath. In recent years, as the airtightness in houses increases, the pollutants are likely to remain indoors, and therefore ventilation needs to be performed at higher rates. However, in buildings located in badly air polluted areas, or houses and offices of members who suffer from pollinosis, people often hesitate to open the windows for ventilation. Hence, air purifiers or air conditioners having an air cleaning function are used. As a method for cleaning the air inside a room, sucking the air in the room and then capturing dust with filters, or adsorbing pollutants with activated carbon is popular.

However, it seems that the effects of the methods including capturing dust with filters or adsorbing pollutants with activated carbon, on modification of the quality of indoor air, are not so significant as compared to the time taken for maintenance such as cleaning and replacement of the filters or activated carbon. The reason for this is that the ion quantity in the air is not included in the subject of adjustment.

Ions are present in the air. It has been recognized that, among the ions, negative ions have the effect of relaxing people. However, negative ions decrease when bonded to specific substances. For instance, if cigarette smoke is present, negative ions sometimes decrease to around ½ to ⅕ of normal amount. Hence, in order to artificially increase the amount of negative ions in the air, an ion generator was developed and is incorporated in a variety of air conditioning apparatuses. By the way, conventional ion generators generate only negative ions by a DC high-voltage system.

Regarding the ion generators, Japanese Laid-Open Patent Publication No. 49-129493 (1974) describes that it is possible to adjust the negative and positive electric potentials according to a desired ratio by a bipolar high voltage generator having mutually separated ionized electrodes and that, in the case of a single transformer, it is possible to separate negative and positive high voltages through high voltage diodes which are connected with the terminals of a high voltage coil so as to face each other, but it fails to describe having two operation modes by a single unit like an ion generator of the present invention.

While Japanese Laid-Open Patent Publication No. 54-40369 (1979) describes the processes of applying an alternating voltage across an induction electrode and an emission electrode to generate an alternating electric field in the space between them, and applying an alternating voltage to an emission electrode assembly which is similar and adjacent to the above electrodes to cause both the emission electrode assemblies to alternately emit unipolar ions, thereby charging fine particles introduced into the space within the alternating electric field, it also fails to describe having two operation modes by a single unit like an ion generator of the present invention.

While Japanese Laid-Open Patent Publication No. 8-217412 (1996) describes that negative ions and positive ions are generated by using a negative electric potential driving power supply and a positive electric potential driving power supply as the power supply to be connected to a corona discharge element, it also fails to describe having two operation modes by a single unit like an ion generator of the present invention.

While Japanese Laid-Open Patent Publication No. 2000-58290 describes control of the frequency of a voltage applied to electrode means and the ON/OFF time of switches that individually control polar voltages, it also fails to describe having two operation modes by a single unit like an ion generator of the present invention.

As described above, with the use of the ion generator, the amount of negative ions in the ion distribution in the air increases, and the air is modified to air quality that relaxes people. However, for the active removal of bacteria floating in the air, negative ions have almost no advantageous effects.

The present invention has been researched in this regard, and found as a result of research that bacteria floating in the air can be removed by simultaneously generating both negative ions and positive ions and emitting them into the air. More specifically, when $H^+(H_2O)_n$ as positive ions and $O_2^-(H_2O)_m$ as negative ions are generated, they react chemically and generate hydrogen peroxide $H_2O_2$ or hydroxyl group radical $(\cdot OH)$ as active species to remove bacteria floating in the air.

However, positive ions have nature to cause stress in human. Therefore, if positive ions and negative ions are generated, the relaxation effect of negative ions is reduced and cancelled. It is thus necessary to switch operation modes according to purposes. In other words, an operation mode of generating substantially equal amounts of positive ions and negative ions is preferred for a bacteria removal/disinfection effect, while an operation mode of generating a larger amount of negative ions compared to positive ions is preferred for a relaxation effect. The reason why generating a small amount of positive ions is to have both the bacteria removal/disinfection effect, which is produced by a combination of a small amount of positive ions and negative ions, and the relaxation effect together.

The present invention has been made with the aim of solving the above problems, and it is an object of the present invention to provide an ion generator capable of switching operation modes as mentioned above, and to provide an air conditioning apparatus incorporating the ion generator.

SUMMARY OF THE INVENTION

An ion generator according to the present invention comprises: first generating means for generating substantially equal amounts of positive ions and negative ions; second generating means for generating a relatively small amount of positive ions and a relatively large amount of negative ions; and switch means for selectively switching to either of the first generating means and the second generating means, wherein the ion generator operates either of the first generating means and the second operating means to which the switch means switches.

In this ion generator, the first generating means generates substantially equal amounts of positive ions and negative ions, and the second generating means generates a relatively small amount of positive ions and a relatively large amount of negative ions. The switch means selectively switches to either of the first generating means and the second generating means, and either of the first generating means and the second operating means to which the switch means switches operates.

Accordingly, it is possible to generate substantially equal amounts of positive ions and negative ions or generate a relatively small amount of positive ions and a relatively large amount of negative ions, and to select a mode of ion generation according to a purpose in such a manner that substantially equal amounts of positive ions and negative ions are generated when the principal aim is to produce a bacteria removal/disinfection effect, and a larger amount of negative ions are generated compared to positive ions when a slight bacteria removal/disinfection effect is desired while aiming principally at producing a relaxation effect.

In an ion generator according to the present invention, the first generating means and the second generating means comprise a dielectric body, a pair of electrodes facing each other with the dielectric body therebetween, and applying means for applying an alternating voltage across the pair of electrodes; the applying means applies an alternating voltage across the pair of electrodes to generate negative ions and positive ions; and the switch means includes a diode having an anode side connected to one of the pair of electrodes, which is not a voltage supply side electrode, and a cathode side to which a common fixed electric potential is applied, and includes switching means connected to both terminals of the diode.

In this ion generator, the first generating means and the second generating means hold a dielectric body between a pair of electrodes, and applying means applies an alternating voltage across this pair of electrodes. By applying an alternating voltage across the pair of electrodes by the applying means, negative ions and positive ions are generated. In the switch means, the anode side of the diode is connected to one of the pair of electrodes, which is not a voltage supply side electrode, a common fixed electric potential is applied to the cathode side, and the switching means is connected to both terminals of the diode.

Accordingly, switching can be performed with a relatively simple circuit structure.

In an ion generator according to the present invention, the diode and the switching means are provided independently from the applying means.

In this ion generator, since the diode and the switching means are provided independently from the applying means, the positioning of the diode and the switching means becomes easier, thereby reducing the manufacturing costs.

An ion generator according to the present invention further comprises timer means, or detecting means for detecting an external environment, wherein the switch means switches based on a time measured by the timer means, or a value detected by the detecting means.

In this ion generator, since the switch means is designed to switch based on the time measured by the timer means, or the value detected by the detecting means for detecting an external environment, it is possible to automatically maintain comfortable air quality in a room.

In an ion generator according to the present invention, the detecting means is a sensor for detecting an air pollution level.

In this ion generator, since the detecting means is a sensor for detecting an air pollution level, it is possible to perform operation in an optimum operation mode according to the air pollution level.

An ion generator according to the present invention further comprises setting means for externally setting the air pollution level, and the switch means switches to the first generating means when the value detected by the sensor is not less than a value set by the setting means, or switches to the second generating means when the detected value is less than the set value.

In this ion generator, the setting means externally sets the air pollution level, and the switch means switches to the first generating means when the value detected by the sensor is not less than a value set by the setting means, or switches to the second generating means when the detected value is less than the set value.

Accordingly, it is possible to perform operation in such a health-oriented manner that, when the air pollution level is high, priority is given to bacteria removal/disinfection, and then, when the air pollution level is lowered, priority is shifted to a relaxation effect.

An ion generator according to the present invention further comprises indicator means for indicating an operational state, and, when the first generating means or the second generating means is in operation, the indicator means indicates its operational state by a corresponding color.

In this ion generator, when the first generating means or the second generating means is in operation, the indicator means indicates its operational state by a corresponding color, and therefore it is possible to know with a single glance whether positive ions having a bacteria removal/disinfection effect are emitted or negative ions having a relaxation effect are mainly emitted.

An ion generator according to the present invention further comprises timer means, and the switch means switches to the first generating means for a predetermined time which is measured from start of operation by the timer means.

In this ion generator, since the switch means switches to the first generating means for a predetermined time which is measured from start of operation by the timer means, it is possible to perform operation in an operation mode of generating substantially equal amounts of positive ions and negative ions, capable of producing a bacteria removal/disinfection effect, at the start of operation, at which time the air is considered dirty.

The ion generator according to the present invention further comprises timer means, and is configured such that the switch means switches to the first generating means for a predetermined time which is measured from start of operation by the timer means, and, after the timer means has measured the predetermined time, the switch means switches based on a pollution level detected by the sensor.

In this ion generator, the switch means switches to the first generating means for a predetermined time which is measured from start of operation by the timer means, and, after the timer means has measured the predetermined time, the switch means switches based on a pollution level detected by the sensor.

Accordingly, it is possible to perform operation in an operation mode of generating substantially equal amounts of positive ions and negative ions, capable of producing a bacteria removal/disinfection effect, for a predetermined time from the start of operation at which time the air is considered dirty, and, after a lapse of the predetermined time, it is possible to switch between the operation mode of generating substantially equal amounts of negative ions and positive ions and an operation mode of generating a larger amount of negative ions, according to the air pollution level.

An air conditioning apparatus according to the present invention comprises means for changing air conditions, and an ion generator according to any of the present invention, wherein negative ions and positive ions generated by the ion generator are changed by the means for changing air conditions and then dispersed into the air.

Accordingly, a bacteria removal/disinfection effect and a relaxation effect are produced in addition to an air conditioning effect inherent to the air conditioning apparatus, thereby making the indoor environment more comfortable.

DESCRIPTION OF THE INVENTION

The following description will explain the present invention with reference to the drawings illustrating some embodiments thereof.

(First Embodiment)

Figure 1:
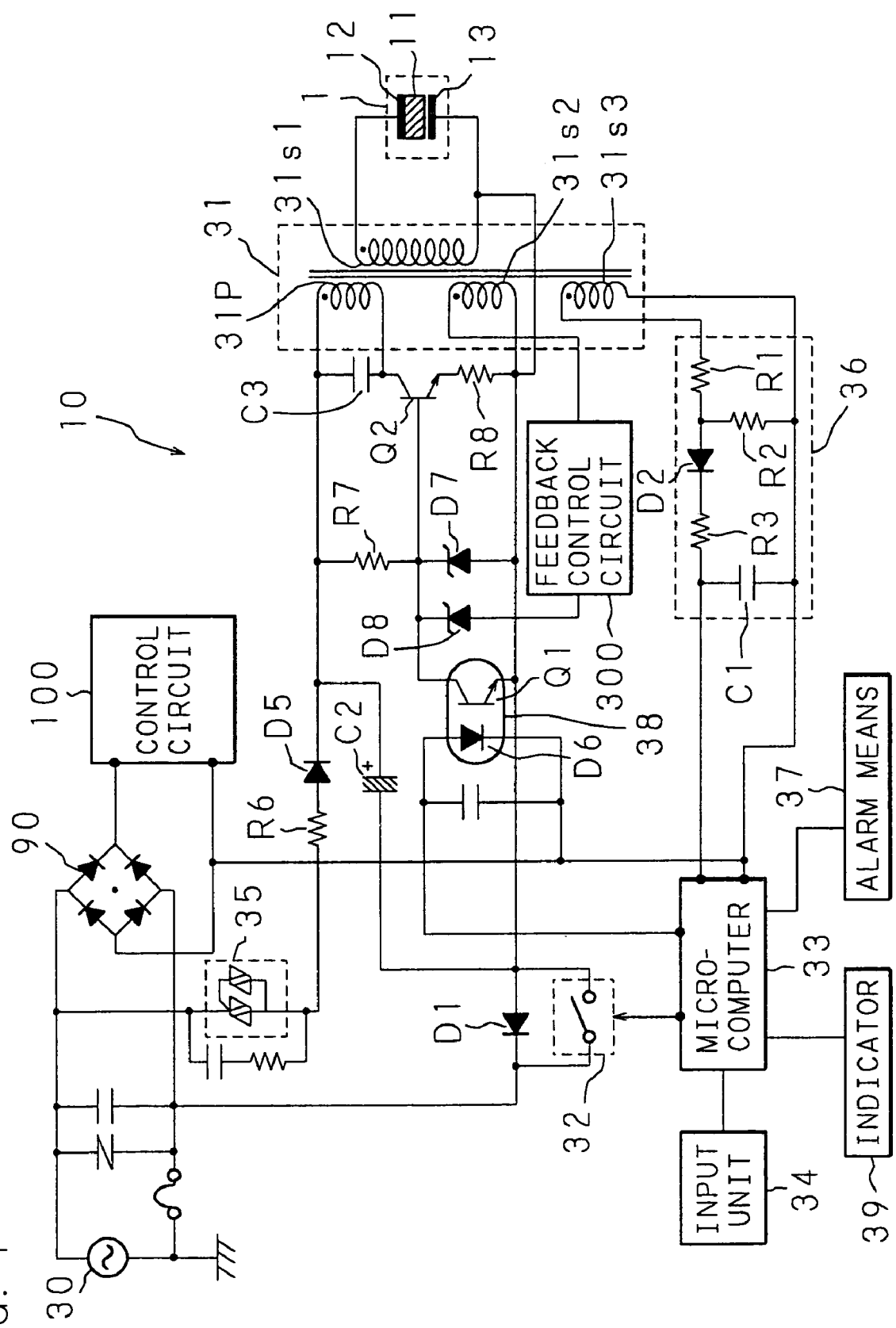
FIG. 1 is a circuit diagram showing one embodiment of an ion generator of the present invention.
Figure 2:
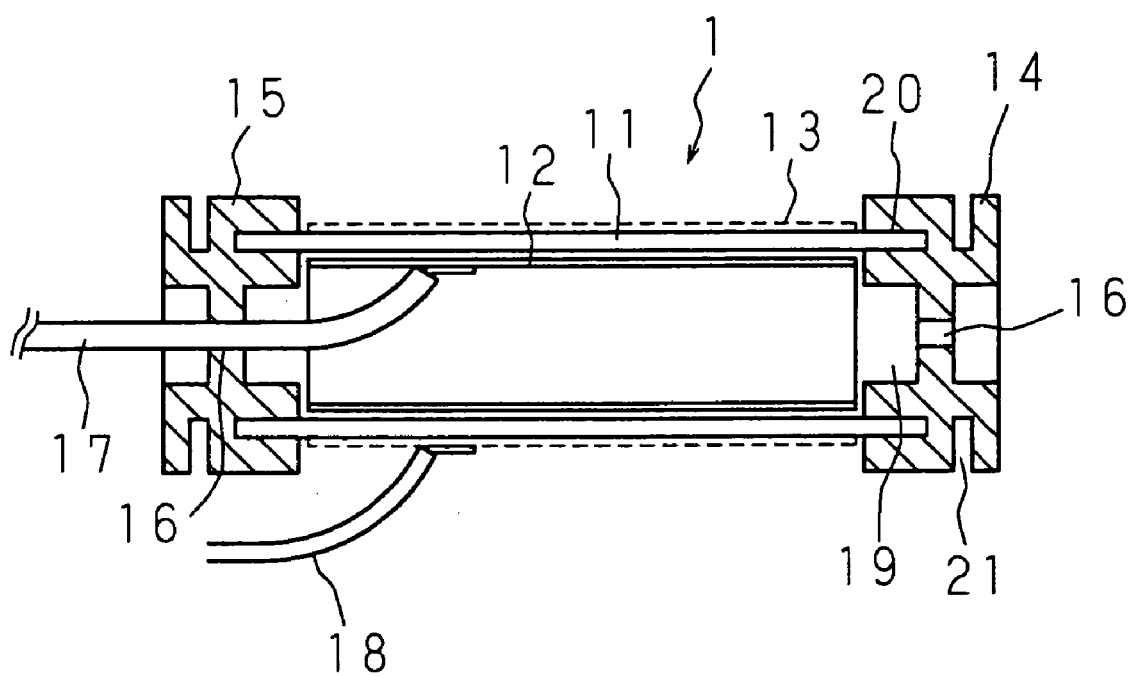
FIG. 2 is a cross sectional view of an ion generating electrode body in the ion generator.
Figure 3:
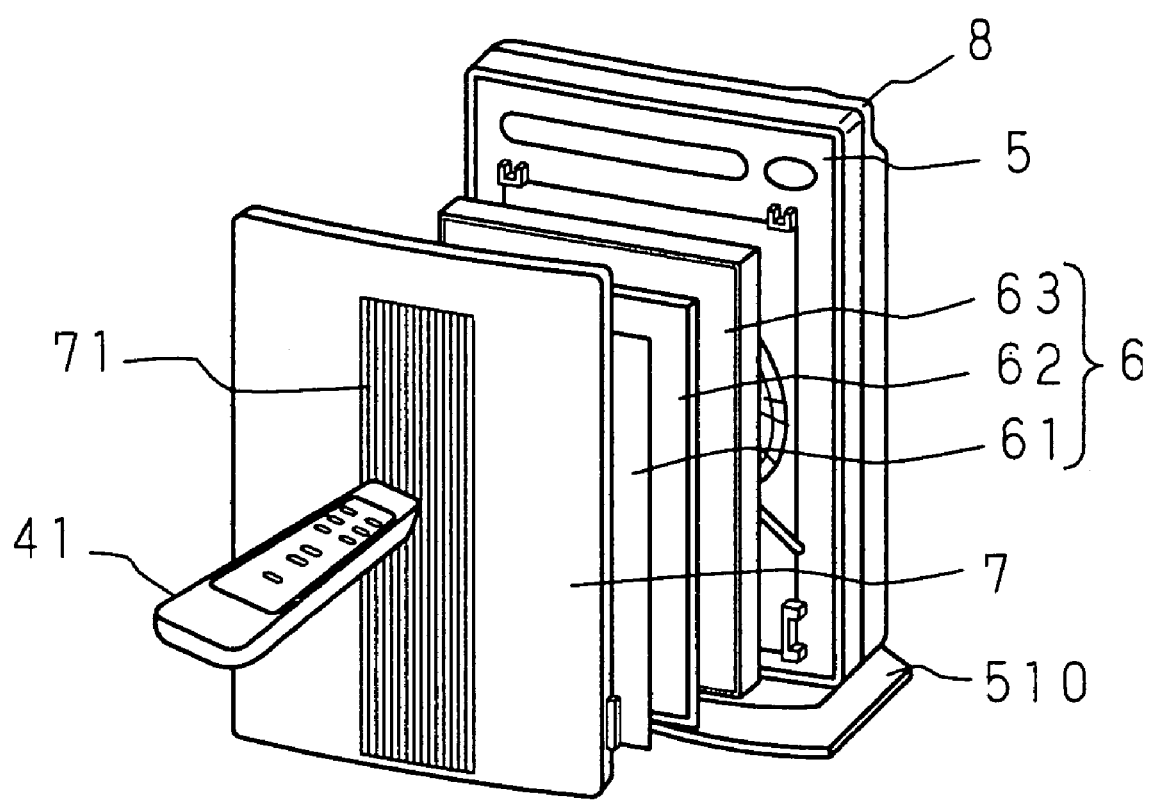
FIG. 3 is an exploded perspective view showing how the front cover and filters are arranged in an air purifier incorporating the ion generator.

Referring to FIG. 1 and FIG. 2, the following description will explain the first embodiment of an ion generator of the present invention.

FIG. 1 is a circuit diagram showing the circuit structure of an ion generator 10. This ion generator 10 includes a rectifier 90 connected to a commercial power supply 30, and a control circuit connected to the output terminal of the rectifier 90. A control circuit 100 is a control circuit of a later-described air conditioning apparatus.

Moreover, the ion generator 10 comprises an ion generating electrode body 1, a switching transformer 31, a relay 32, a microcomputer 33, an input unit 34 of the microcomputer 33, an SSR 35 (Solid State Relay), a malfunction detection circuit 36, an alarm means 37, a photocoupler 38, an indicator 39, and a feedback control circuit 300.

The switching transformer 31 includes a primary winding 31$p$, and secondary winding 31$s$1, 31$s$2 and 31$s$3. The secondary winding 31$s$1 is provided to apply an alternating high voltage to a later-described ion generating electrode body. The SSR 35 which is connected to the commercial power supply 30 in parallel with the rectifier 90 is connected to the primary winding 31$p$. A resistor R6 and a diode D5 are inserted in series between the SSR 35 and one terminal of the primary winding 31$p$. The diode D5 is positioned so that the anode side is connected to the SSR 35 and the cathode side is connected to the one terminal of the primary winding 31$p$. The other terminal of the primary winding 31$p$ is connected to the collector of an npn-type switching transistor Q2. Moreover, a capacitor C3 is connected across the two terminals of the primary winding 31$p$. The emitter of the switching transistor Q2 is connected to the commercial power supply 30 through a resistor R8 and a diode D1. The diode D1 is positioned so that the anode side is connected to the primary winding 31$p$ and the cathode side is connected to the commercial power supply 30. Note that one side of the commercial power supply 30 to be connected to the diode D1 is grounded. In addition, the relay 32 is connected to the diode D1 in parallel.

The positive side of a capacitor C2 is connected to the cathode side of the diode D5, while the negative side is connected to the anode side of the diode D1.

The base of the switching transistor Q2 is connected to the cathode side of the diode D5 through a resistor R7, and also connected to the anode side of the diode D1 through a zener diode D7. The emitter of the switching transistor Q2 is connected to the negative side of the secondary winding 31$s$2 of the switching transformer 31 through the resistor R8. The positive side of the secondary winding 31$s$2 is connected to one terminal of the feedback control circuit 300, and the other terminal of the feedback control circuit 300 is connected to the base of the switching transistor Q2 through a zener diode D8.

The photocoupler 38 is composed of an npn-type phototransistor Q1 and a light emitting diode D6 to be optically coupled with the phototransistor Q1. The collector of the phototransistor Q1 is connected to the junction of the resistor R7 and the zener diode D7, while the emitter is connected to the negative side of the capacitor C2. Both terminals of the light emitting diode D6 are connected to the microcomputer 33.

The ion generating electrode body 1 is connected between the positive electrode and negative electrode of the secondary winding 31$s$1 of the switching transformer 31. The ion generating electrode body 1 is composed mainly of a dielectric body, and a pair of electrodes facing each other with the dielectric body therebetween. In this embodiment, as shown in FIG. 2, a cylindrical glass tube with both ends open ("Pyrex" (trade name): 20 mm outer diameter) 11 is used as the dielectric body. The material of the dielectric body is not limited to this, and any material can be used if it has an insulating property. Moreover, the shape is not limited, and is suitably determined by considering the shape and structure of an apparatus to be installed. If the dielectric body has a circular shape as in this embodiment, the larger the outer diameter and the thinner the thickness, the larger the electrostatic capacity and thereby facilitating ion generation. However, since the generation of ozone increases at the same time, it is necessary to determine the dimensions by taking the balance between ions and ozone into account. According to the results of experiments, an outer diameter of not more than 20 mm and a thickness of not more than 1.6 mm are recommended for the glass tube 11.

An internal electrode 12 and an external electrode 13, both of which have a shape created by rolling a stainless plain weave wire mesh into a cylindrical shape, are placed inside and outside of the glass tube 11. The internal electrode 12 functions as a high voltage electrode, while the external electrode functions as a ground electrode. For the internal electrode 12, one obtained by rolling a 40-mesh plain weave wire mesh made of stainless steel wires of SUS316 or SUS304 into a cylindrical shape is used. For the external electrode 13, similarly, one obtained by rolling a 16-mesh plain weave wire mesh made of stainless steel wires of SUS316 or SUS304 into a cylindrical shape is used. Note that "mesh" means the number of wires per inch. Accordingly, the larger the mesh number, the finer the mesh. Note that, in order to increase the electrostatic capacity of the ion generating electrode body 1 and improve the ion generation efficiency, the internal electrode 12 and the external electrode 13 are adhered to the glass tube 11.

Both ends of the glass tube 11 are closed with insulating plug members 14 and 15. The plug members 14 and 15 are formed using an elastic material like rubber. Each of the plug members 14 and 15 is substantially cylindrical, and has a circumferential protruding part 19 on one side and a circumferential groove 20 formed in the circumferential protruding part 19 so that the ends of the glass tube 11 are inserted into the circumferential grooves 20. Moreover, in the outer circumferential surface of each of the plug members 14 and 15, an outer circumferential groove 21 is formed. The outer circumferential grooves 21 are used to fix the ion generating electrode body 1 to the air conditioning apparatus.

A hole 16 covered with a thin film is formed in the center of each of the plug members 14 and 15. The thin film was processed in such a manner as to be easily torn, so that an object can be inserted by breaking though the thin film, if necessary. In this embodiment, a lead wire 17 is passed through the hole 16 of the plug member 15. The lead wire 17 is connected to the internal electrode 12 inside the glass tube 11. In addition, a lead wire 18 is connected to the external electrode 13.

The ion generating electrode body 1 is assembled as follows. First, the internal electrode 12 to which the lead wire 17 was welded beforehand is inserted into the glass tube 11. Subsequently, the thin film of the hole 16 of the plug member 15 is broken by a tool with a sharp point to pass the lead wire 17 through this hole 16, and then the plug member 15 is fitted to the glass tube 11. Next, the external electrode 13 to which the lead wire 18 was welded beforehand is fitted around the outside of the glass tube 11, and then the plug member 14 is fitted to the other end of the glass tube 11.

Note that the external electrode 13 which is not a voltage supply side electrode is connected to the anode side of the diode D1 as shown in FIG. 1.

The malfunction detection circuit 36 is connected between the positive electrode and negative electrode of the secondary winding 31$s$3 of the switching transformer 31. The malfunction detection circuit 36 is composed of resistors R1, R2, R3, diode D2 and capacitor C1, and these elements are connected as follows. First, the resistor R1, diode D2 and resistor R3 are connected in series to the positive side of the secondary winding 31$s$3. The diode D2 is positioned so that the anode side is connected through the resistor R1 to the positive side of the secondary winding 31$s$3, while the cathode side is connected to one terminal of the resistor R3. The resistor R2 is connected between the other terminal of the secondary winding 31$s$3 and the junction of the anode side of the diode D2 and the resistor R1, and the capacitor C1 is connected between the other terminal of the resistor R3 and the negative side of the secondary winding 31$s$3. The malfunction detection circuit 36 configured in such a manner is connected to the microcomputer 33.

Next, the function of the ion generator 10 will be explained.

An alternating voltage outputted from the commercial power supply 30 is converted into a direct current rectified and smoothed by the diode D5 and the capacitor C2. This direct current is supplied to the primary winding 31$p$ of the switching transformer 31 when the switching transistor Q2 is turned on. The feedback control circuit 300 controls ON/OFF of the switching transistor Q2, based on the induced voltage of the secondary winding 31$s$2 of the switching transformer 31. Accordingly, a high voltage is generated in a stable manner in the secondary winding 31$s$1.

The microcomputer 33 controls the on/off state of the relay 32, based on a signal from its input unit 34. When the relay 32 is in the on state, the external electrode 13 is grounded without the diode D1. Further, a sinusoidal voltage is applied to the internal electrode 12. This state is a "first operation mode".

When an alternating voltage is applied across the electrodes 12 and 13 facing each other with the glass tube 11 therebetween as described above, an ionization phenomenon such as discharge occurs in the atmosphere, and substantially equal amounts of positive ions and negative ions are generated.

At this time, $H^+(H_2O)_n$ and $O_2^-(H_2O)_m$ are generated as positive ions and negative ions, respectively, in the most stable manner. These positive ions and negative ions do not independently have significant bacteria removal effects against bacteria floating in the air. However, when these ions are generated, hydrogen peroxide $H_2O_2$ or hydroxyl group radical (—OH) as active species are produced by chemical reaction. Since $H_2O_2$ or (—OH) has extremely strong activity, it is possible to remove or kill bacteria in the air by emitting these ions into the air.

When the relay 32 is turned off, the "second operation mode" takes place. At this time, electrons flow in the route of ground→diode→D1→secondary winding 31$s$1→internal electrode 12→glass tube 11→air→ground, and electrons are emitted into the air between the internal electrode 12 and the external electrode 13, and consequently negative ions are generated. At this time, since electrons do not flow in the route of glass tube 11→internal electrode 12→secondary winding 31$s$1→diode D1→ground, the internal electrode 12 can never receive electrons from the air between the electrodes. However, since the loop of external electrode 13→glass tube 11→internal electrode 12→secondary winding 31$s$1→external electrode 13 is formed, a small amount of positive ions are generated. Therefore, when the relay 32 is in the off state, the ion generating electrode body 1 produces a relatively large amount of negative ions and a relatively small amount of positive ions from the air. At this time, the ratio of generation of negative ions to positive ions is about 4:1 to 6:1 and the amount of negative ions is much larger, and thus a relaxation effect can be obtained.

The microcomputer 33 also controls the on/off state of the SSR 35, based on a signal from the input means 34. When the SSR 35 is turned on, the ion generating electrode body 1 is turned into an operational state, while, when the SSR 35 is turned off, the ion generating electrode body 1 is turned into a non-operational state. The indicator 39 is used to indicate the operational state of this ion generating electrode body 1.

The malfunction detection circuit 36 operates as follows. An induced voltage corresponding to the voltage across the terminals of the secondary winding $31s1$ is generated in the secondary winding $31s3$. This induced voltage is rectified and smoothed, and then inputted to the microcomputer 33. When a short circuit develops between the electrodes of the ion generating electrode body 1, the voltage of the secondary winding $31s3$ is also in a short state (=0 V). Therefore, a voltage signal to be inputted to the microcomputer 33 becomes smaller than usual. On the other hand, when the internal electrode 12 or the external electrode 13 is disconnected, the induced voltage of the secondary winding $31s3$ becomes higher than usual. Accordingly, a voltage signal to be inputted to the microcomputer 33 is larger than usual.

As described above, if a voltage signal deviating from its normal level is inputted to the microcomputer 33, the microcomputer 33 judges that something abnormal happened to the ion generating electrode body 1, and actuates the alarm means 37. The alarm means 37 informs the user of the abnormality by means of light, sound, characters, etc.

(Second Embodiment)

Next, the following description will explain incorporating an ion generator 10 into an air conditioning apparatus.

FIG. 3 through FIG. 12 show an air purifier which is taken as one example of the air conditioning apparatus. The air purifier comprises a main body 5 having a shape like a flat box standing vertically, a base 510 supporting the main body 5, and a front cover 7 attached to one side of the main body 5 (the front face in this case) with a space between the front cover 7 and the main body 5. The front face of the main body 5 is curved moderately to have a convex center when seen from the top, and the front cover 7 is also curved to have a convex center, in a corresponding manner, when seen from the top. An air inlet 71 configured by arranging a plurality of vertically long slits side by side is formed in the center of the front cover 7. Moreover, the clearance between the four edges of the front cover 7 and the main body 5 functions as a side-face air inlet 72 (see FIG. 6).

Figure 5:
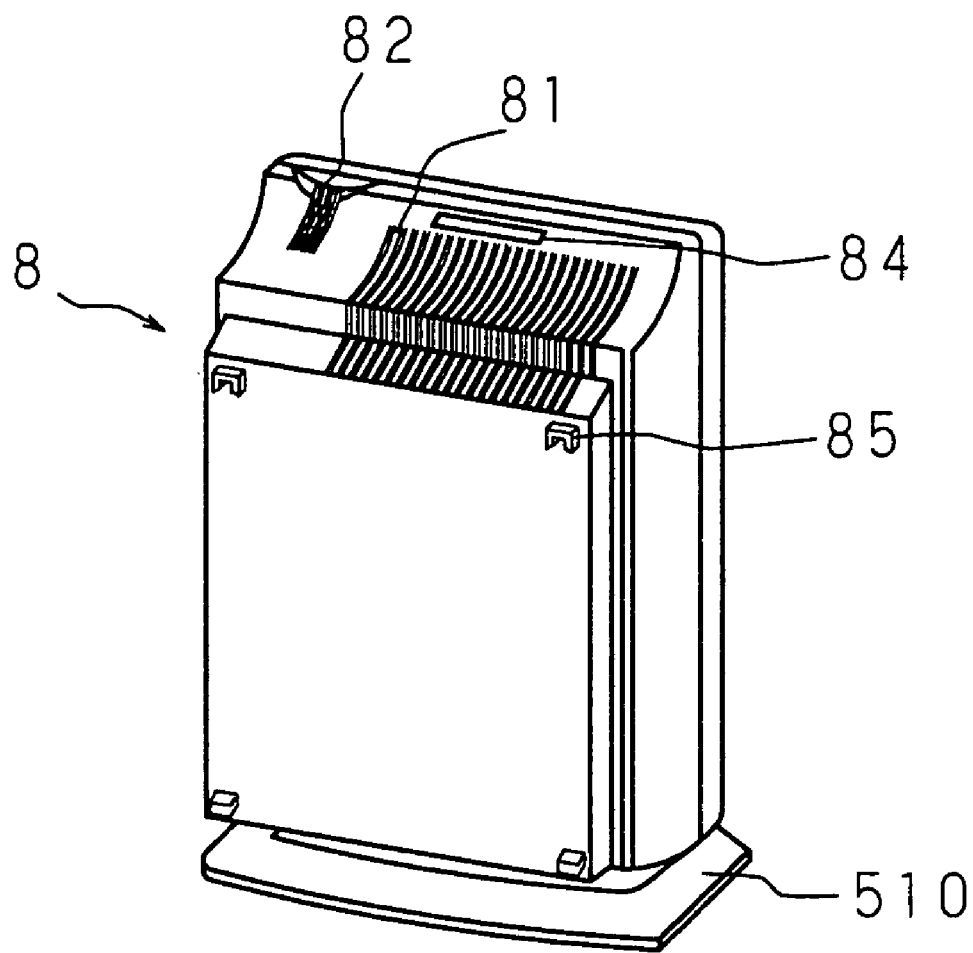
FIG. 5 is a rear perspective view of the air purifier.
Figure 6:
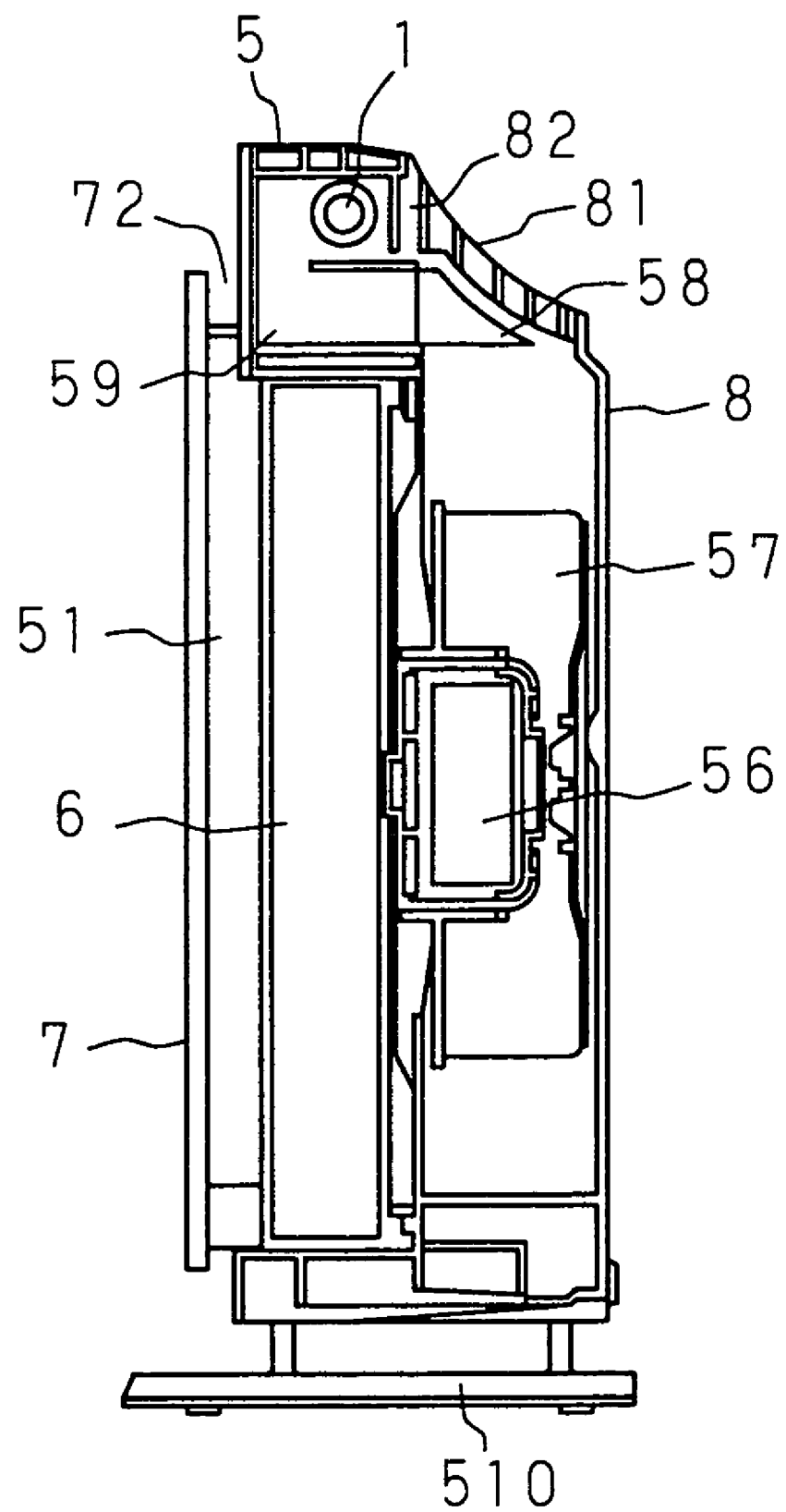
FIG. 6 is a vertical cross sectional view of the air purifier.

The rear face section of the main body 5 is composed of a rear cover 8. As shown in FIG. 5, an air outlet 81 and an ion outlet 82 are formed in the top section of the rear cover 8. Both of the air outlet 81 and ion outlet 82 are configured by arranging a plurality of vertically long slits side by side. A grip 84 is formed of a rectangular recessed part, and wall mount holes 85 are formed for mounting the main body 5 on a wall with separately prepared wall mount metal fittings (not shown).

Figure 7:
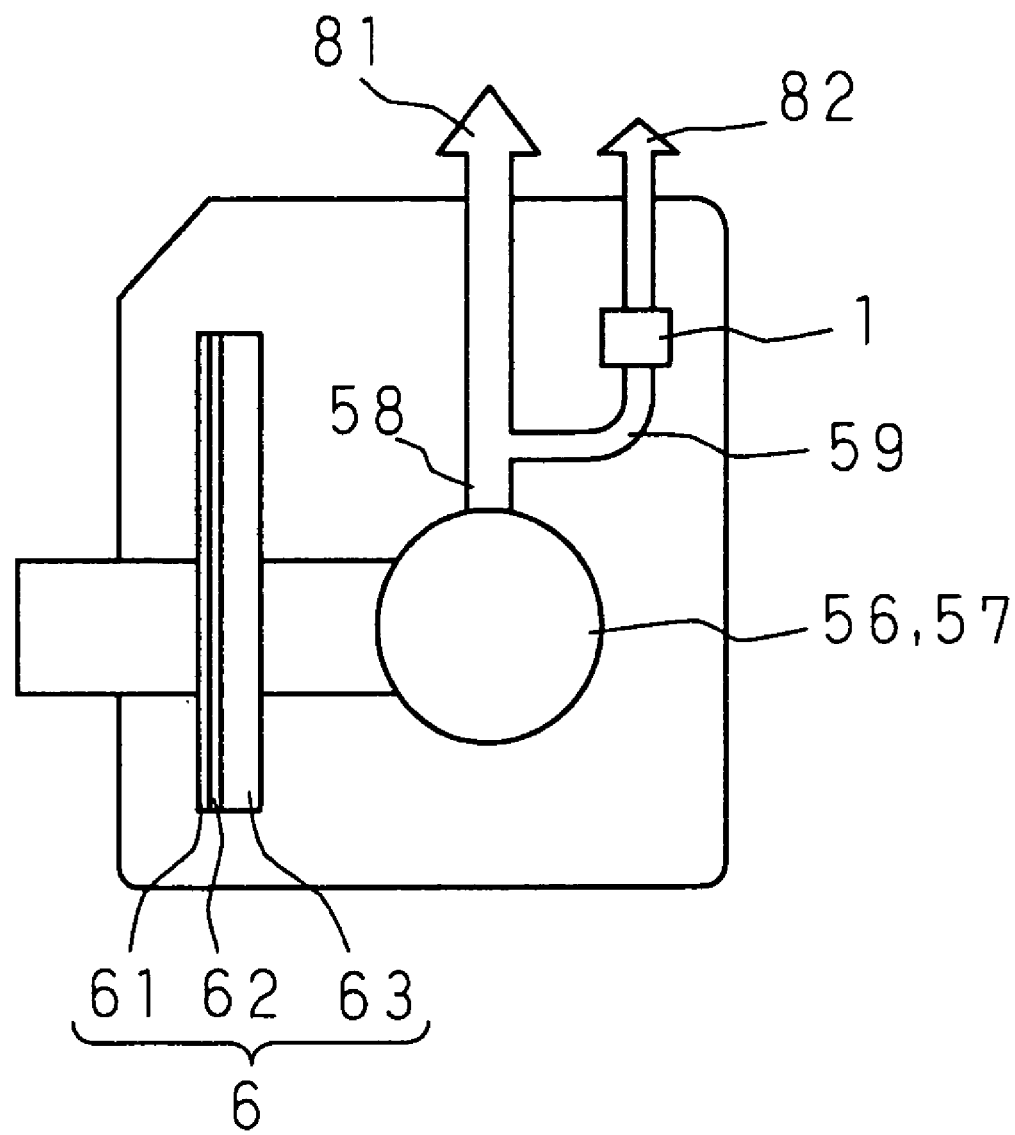
FIG. 7 is a schematic view for explaining the flow of air inside the air purifier.
Figure 8:
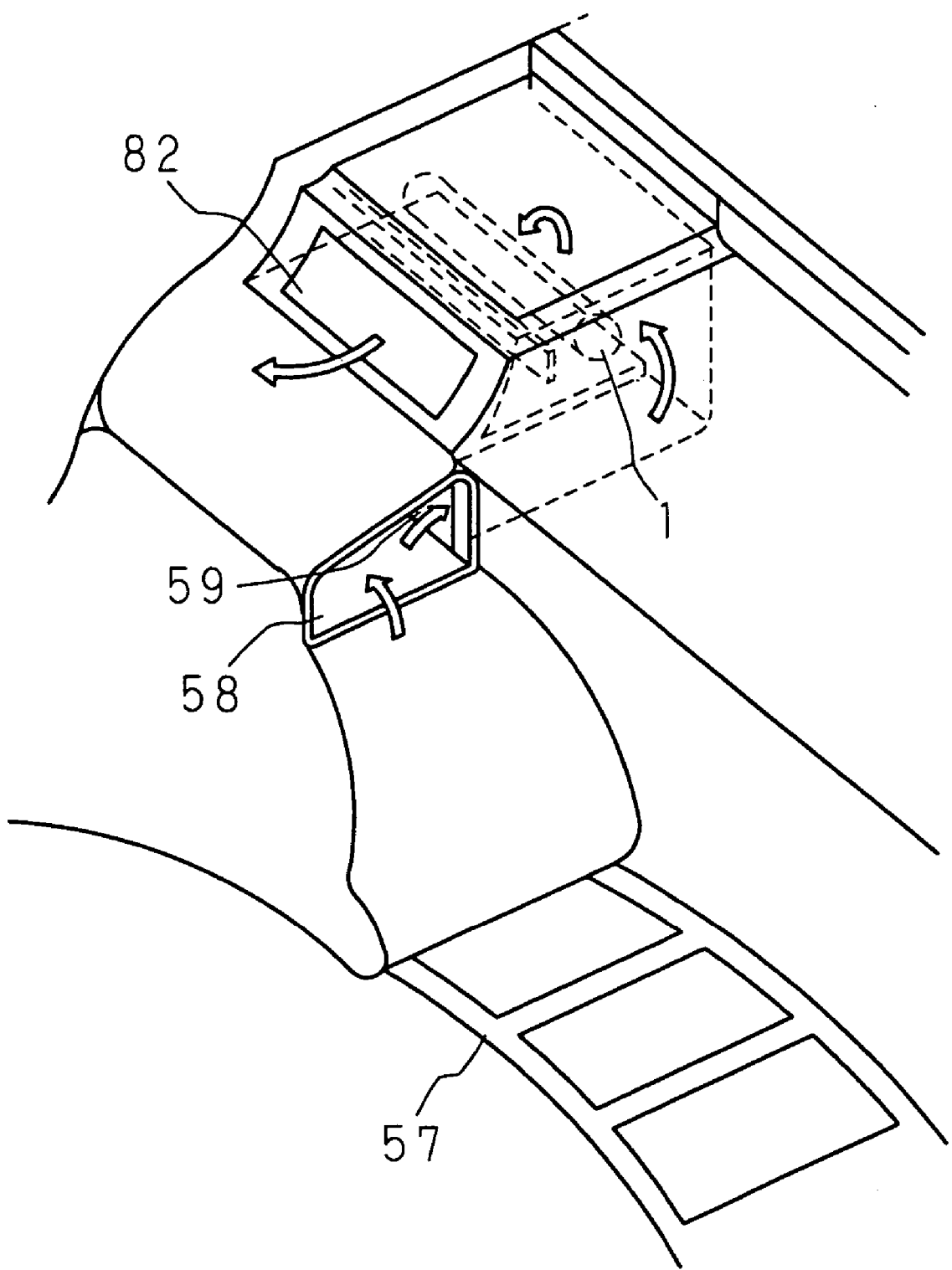
FIG. 8 is a partial perspective view showing the internal structure of the air purifier.

FIG. 7 schematically shows the arrangement of the main components and the flow of air inside the main body 5. 6 represents a filter, and 56 and 57 are a fan motor and a fan. When the fan 57 is rotated by the fan motor 56, air is sucked from the air inlet 71 and the side-face air inlet 72. When the air reaches the fan 57 through the filter 6, it changes the direction toward upward and flows to the air outlet 81. On the way to the air outlet 81, an air passage 58 branches out into a bypass passage 59 running to the ion outlet 82. The ion generating electrode body 1 is placed in the bypass passage 59.

Figure 4:
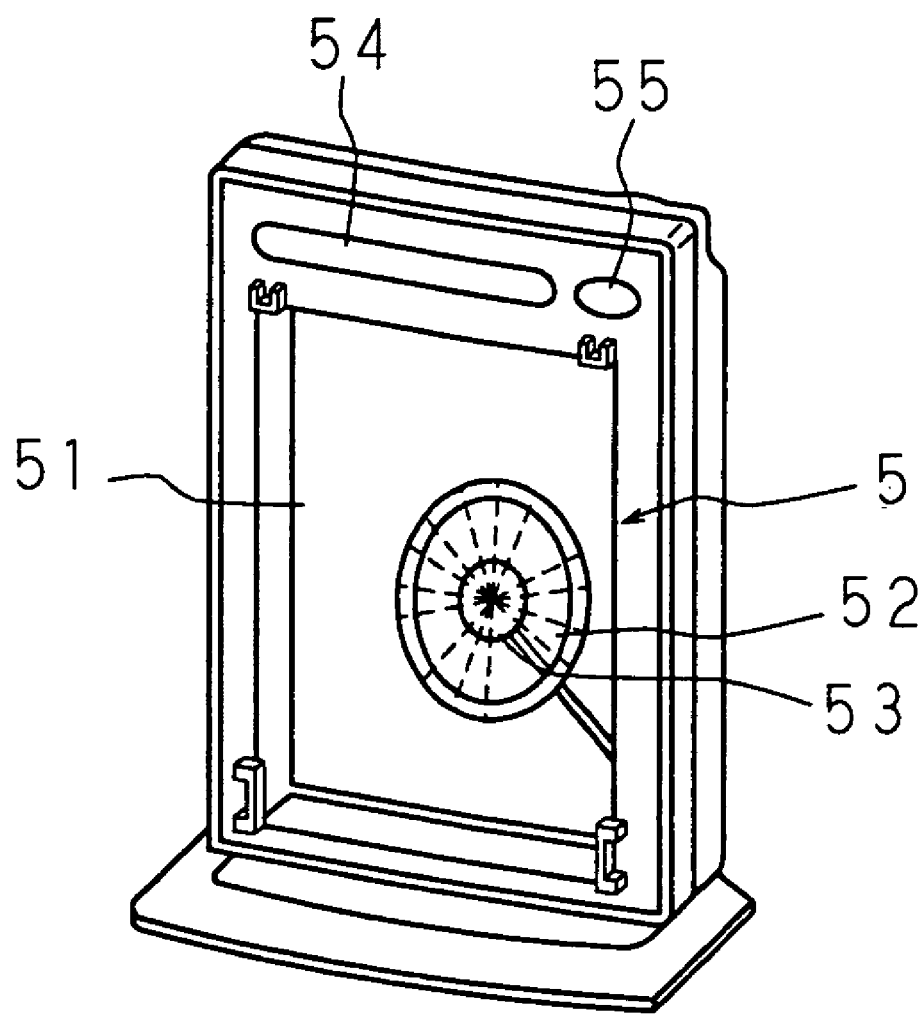
FIG. 4 is a perspective view of the air purifier from which the front cover and filters are removed.

As shown in FIG. 4, a storage section 51 is formed in the front face of the main body 5 to store the filter 6 therein. The filter 6 is composed of three kinds of filters, namely a pre-filter 61, a deodorizing filter 62, and a dust collecting filter 63 from the upstream side of the intake air flow.

The pre-filter 61 is made of polypropylene, and captures relatively large dust from the sucked air. The deodorizing filter 62 is configured in three-layer structure by attaching a non-woven polyester fabric to a rectangular frame, evenly spreading activated carbon on the fabric and further placing a non-woven polyester fabric thereon, and it absorbs a smelling component in the air, such as acetaldehyde, ammonia and acetic acid. The dust collecting filter 63 is a so-called HEPA filter produced by using an aggregate made of polyester/vinylon based non-woven fabric and an electret meltblown non-woven fabric ("Toraymicron" (trade name) available from Toray Industries, Inc.) together as a filter material, folding the filter material, placing a non-woven hydroxy-apatite antibacterial sheet on both the upper and lower faces of the filter material, bonding them by thermocompression bonding, and welding a frame made of a non-woven fabric with hot-melt, and it captures minute dust.

A ventilation opening 52 running to the fan 57 is formed in a vertical wall behind the storage section 51. The ventilation opening 52 is configured by arranging a number of elongated holes radially. A recessed section 53 is formed at the center of the ventilation opening 52, the fan motor 56 is attached to the rear face side of the recessed section 53, and the fan 57 is attached to the rotation shaft of the fan motor 56.

As the fan 57, a turbofan is illustrated in the drawing, but the type of the fan is not necessarily limited to this. It is possible to use a propeller fun or cross flow fan. The turbofan illustrated in the drawing is designed to have a large thickness compared to the fan diameter so as to decrease the rotation speed and the noise level. A DC motor is employed for the fan motor 56 by placing greater importance on controllability.

Most of air sent from the fan 57 is blown out from the air outlet 81 via the air passage 58, but a part of the air passes through the bypass passage 59, receives ions generated by the ion generating electrode body 1 and is blown out from the ion outlet 82.

When ions are generated by application of an alternating high voltage to the electrodes, ozone is generated as a by-product. Naturally, ozone gradually decomposes into oxygen, but the decomposition is further promoted by the presence of an ozone decomposing catalyst. It is therefore preferable to cause at least one of the glass tube 11, the internal electrode 12 and external electrode 13 to carry an ozone decomposing catalyst, or position a separately prepared catalyst carrier adjacent to the ion generating electrode body 1, to promote the decomposition of the generated ozone into oxygen and reduce the amount of ozone. As the ozone decomposing catalyst, it is possible to use conventionally known manganese dioxide, platinum, lead dioxide, copper(II) oxide, and nickel. If a catalyst carrier is to be prepared separately, it is preferable to prepare a base body made of a cylindrical wire mesh and arrange the base body outside of the external electrode 13 concentrically with a predetermined space therebetween.

In order to cause the base body to carry an ozone decomposing catalyst, it is preferable to disperse the ozone decomposing catalyst into a binder substance and attaching the dispersion to the base body surface by coating means such as dipping, spinning and spraying. The amount of the ozone decomposing catalyst to be carried is suitably determined from the amount of ozone generated.

Figure 9:
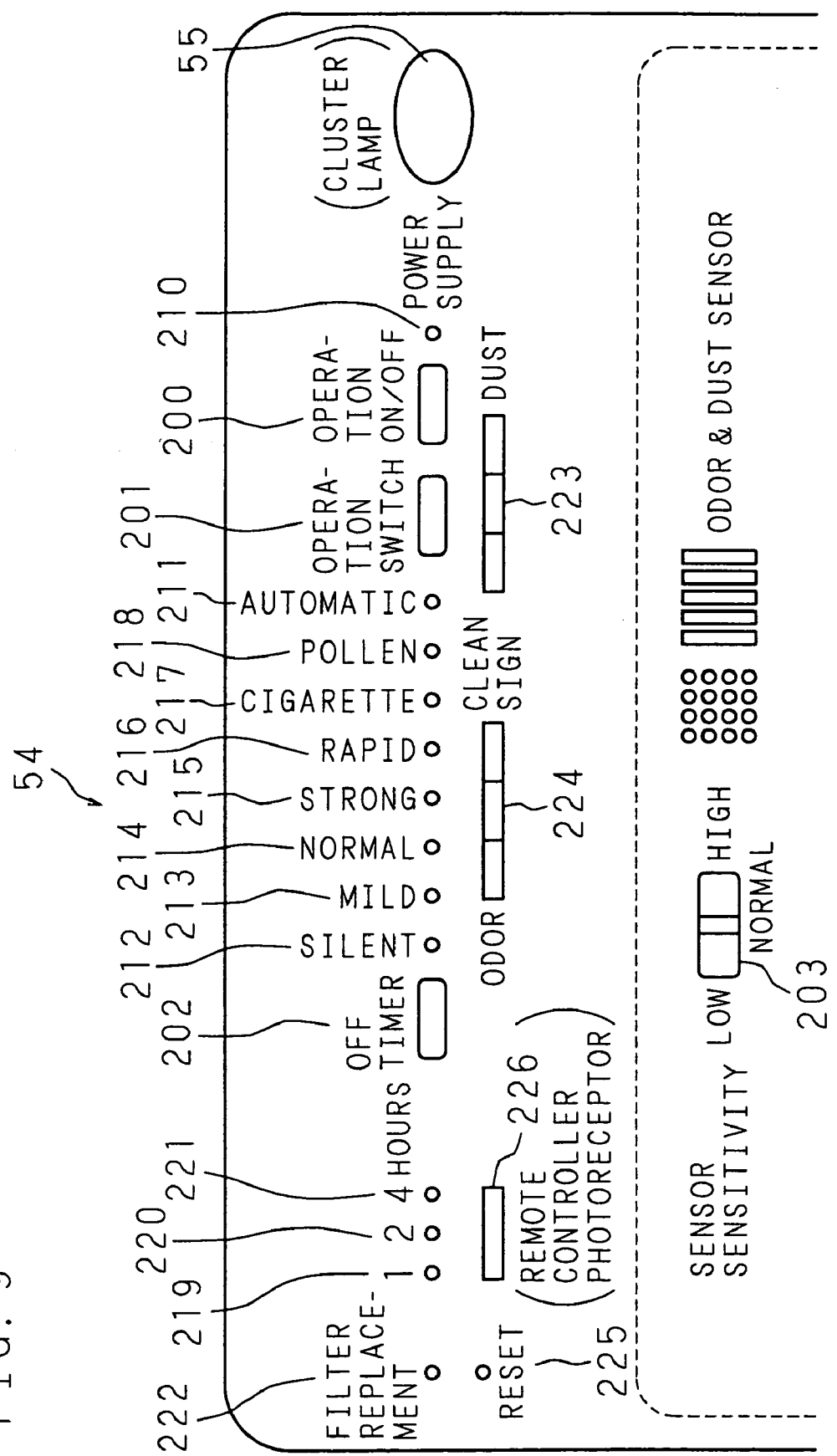
FIG. 9 is a front view of the operating unit of the air purifier.

The top of the front face of the main body 5 is an control unit 54. In the control unit 54, as shown in FIG. 9, various buttons and controller of switches, and indicator lamps are arranged. 200 is an "Operation On/Off" button, 201 is an "Operation Switch" button, 202 is an "Off Timer" button, and 203 is a sensor sensitivity switch controller. 210 is a "Power Supply" lamp, 211 is an "Automatic Operation" lamp, 212 is a "Silent Operation" lamp, 213 is a "Mild Operation" lamp, 214 is a "Normal Operation" lamp, 215 is a "Strong Operation" lamp, 216 is a "Rapid Operation" lamp, 217 is a "Cigarette Operation" lamp, 218 is a "Pollen Operation" lamp, 219 is a "1-hour" lamp, 220 is a "2-hour" lamp, and 221 is a "4-hour" lamp. 222 is a "Filter Replacement" lamp, 223 is a dust sensor lamp, and 224 is an odor sensor lamp. These lamps are composed of light emitting diodes. 225 is a filter reset button, and 226 is a remote controller photoreceptor.

A view window 55 is provided on the right side of the control unit 54. The view window 55 is located at a position facing the ion generating electrode body 1 for confirmation of the operational state of the ion generating electrode body 1. The view window 55 is covered with a light transmitting plastic, so that a finger can not be inserted. A lamp is installed inside the view window 55, and it is named "Cluster Lamp". The "Cluster Lamp" is composed of a plurality of light emitting diodes that emit light of different colors, and emits different colors according to generation state of a group of ions or the ion clusters. The user can know the operational state of the ion generating electrode body 1 by seeing the color of light emitted through the view window 55.

Figure 10:
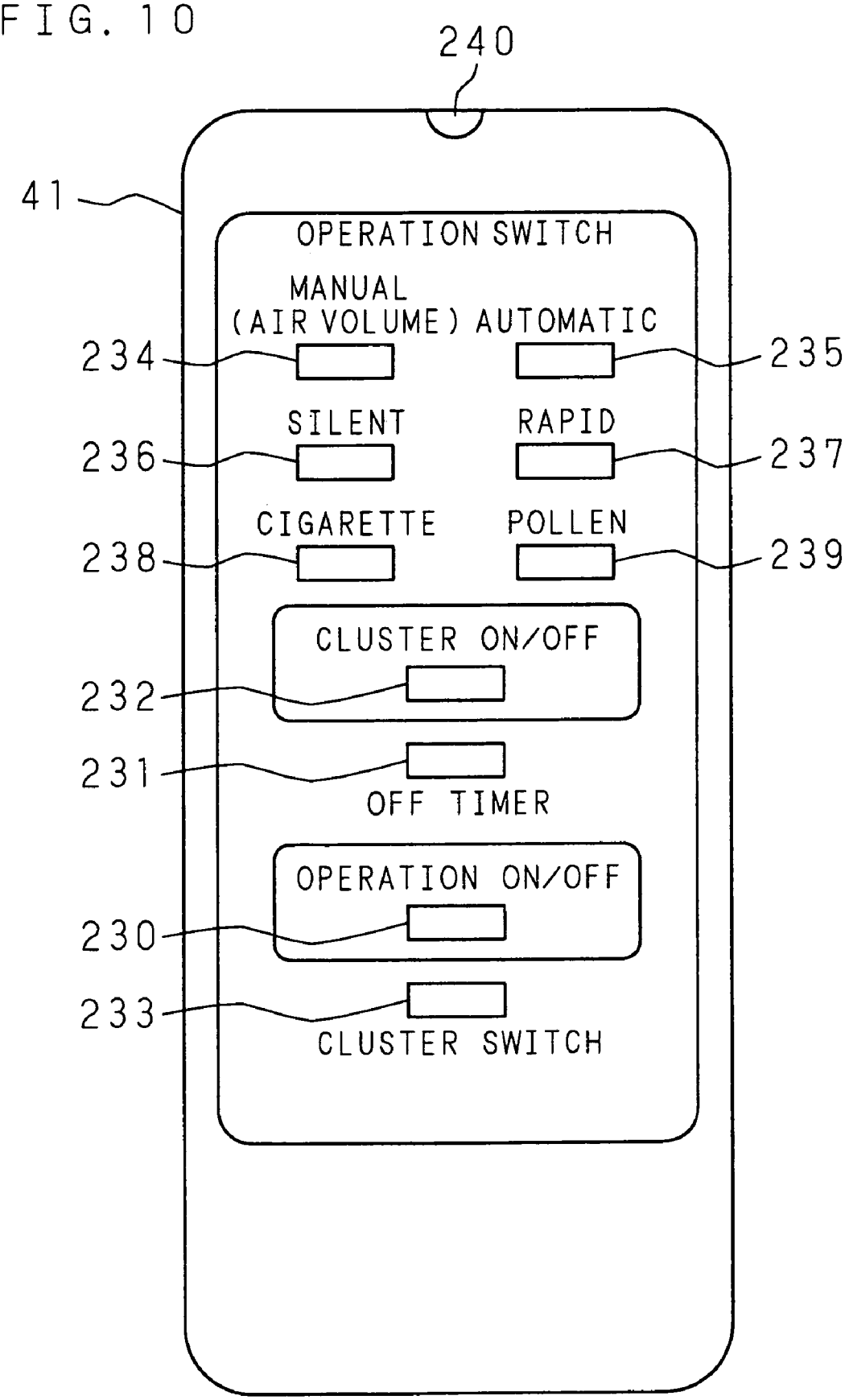
FIG. 10 is a front view of the remote controller of the air purifier.

The remote controller 41 comprises a variety of switches (buttons of the switches) as shown in FIG. 10. 230 is an "Operation On/Off" button, 231 is an "Off Timer" button, 232 is a "Cluster On/Off" button, and 233 is a "Cluster Switch" button. 234 is a "Manual Operation (Air Volume)" button, 235 is an "Automatic Operation" button, 236 is a "Silent Operation" button, 237 is a "Rapid Operation" button, 238 is a "Cigarette Operation" button, and 239 is a "Pollen Operation" button. Provided at the top end of the remote controller 41 is a transmitter 240 for transmitting an infrared signal to the remote controller photoreceptor 226.

Figure 11:
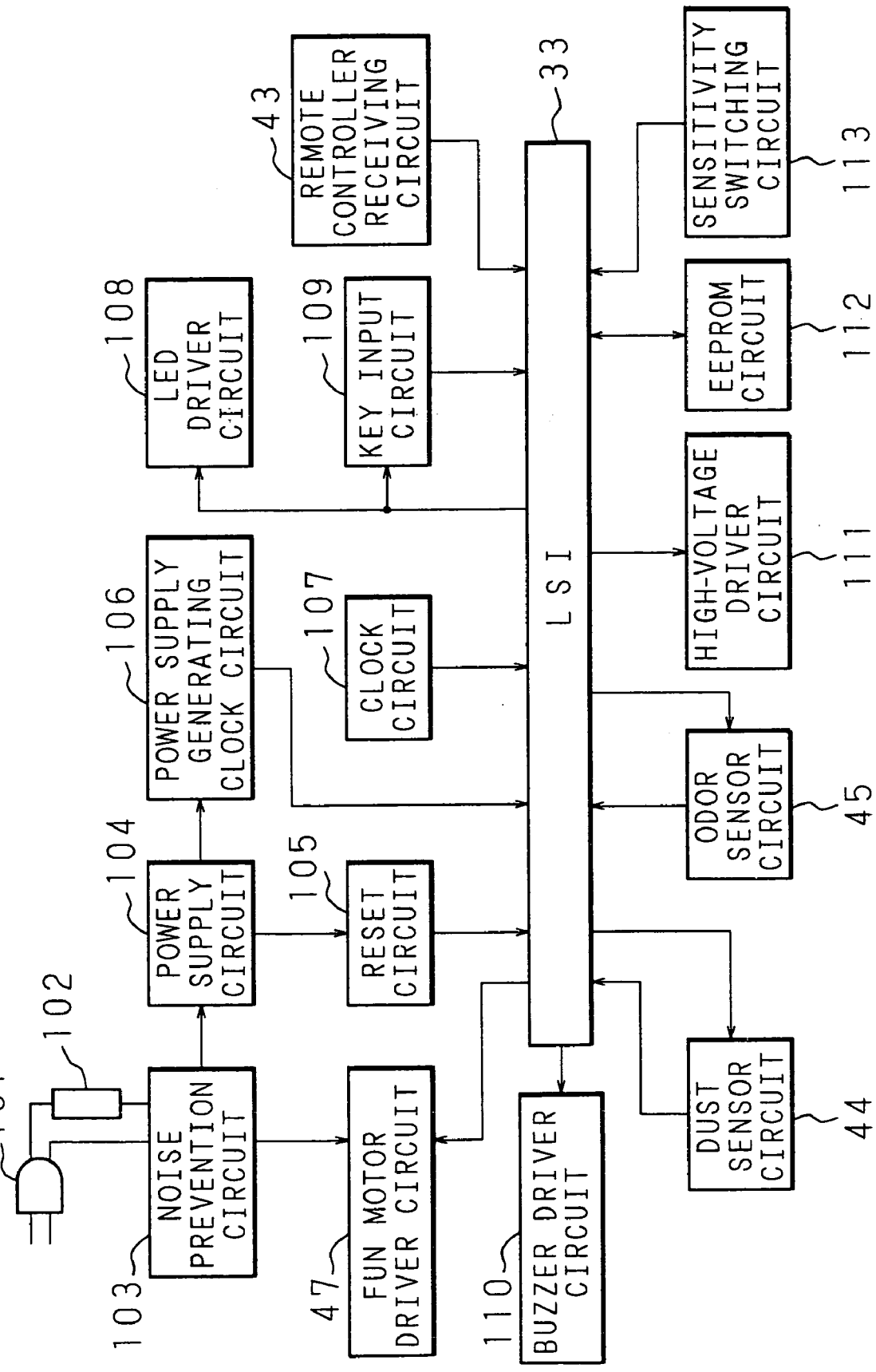
FIG. 11 is a block diagram showing the circuit structure of the air purifier.

The control circuit 100 of the air purifier is configured as shown in FIG. 11. The main component of the control function is the microcomputer 33 (LSI) which is also shown in FIG. 1, and the following elements are coupled with the microcomputer 33. 101 is a plug to be connected to the commercial power supply 30, 102 is a fuse, 103 is a noise prevention circuit, 104 is a power supply circuit, and 105 is a reset circuit. 106 is a power supply generating clock circuit, 107 is a clock circuit, 108 is an LED driver circuit, and 109 is a key input circuit. 43 is a remote controller receiving circuit, 47 is a fan motor driver circuit, 110 is a buzzer driver circuit, 44 is a dust sensor circuit, 45 is an odor sensor circuit, 111 is a high-voltage driver circuit, 112 is an EEPROM circuit, and 113 is a sensitivity switching circuit.

The noise prevention circuit 103 protects the circuit from external noise and lightning surge entering from the plug 101, and absorbs noise going outside. The power supply circuit 104 contains a rectifier 90 and a rectifier circuit composed of the diode D5 and capacitor C2, and supplies a current to those that require power, such as the microcomputer 33, switching transformer 31, fan motor 56, lamps, buzzers and sensors. The reset circuit 105 resets the microcomputer 33 when the voltage supplied to the microcomputer 33 is lower than a set value. The power supply generating clock circuit 106 converts the primary voltage waveform of the power supply circuit 104 into a square wave signal. The clock circuit 107 generates a clock signal necessary for the operation of the microcomputer 33. The LED driver circuit 108 turns on LEDs that constitute lamps.

When the buttons of various switches are pressed or a controller is moved, the key input circuit 109 inputs the corresponding signals to the microcomputer 33. The buzzer driver circuit 110 turns on the buzzer to make sound. The high-voltage driver circuit 111 inputs 100 V AC to the switching transformer 31, which is a high-voltage unit, to generate a high voltage of about 1.8 kV AC. The EEPROM circuit 112 writes, into the EEPROM, the accumulated operation time of the fan motor 56. Upon the manipulation of the sensor sensitivity switching controller 203, the sensitivity switching circuit 113 changes the sensitivity of the dust sensor and the odor sensor among three levels (High, Middle, Low).

The fan motor driver circuit 47 controls the fan motor 56 by PWM control. The remote controller receiving circuit 43 receives an infrared signal from the remote controller 41 through the remote controller photoreceptor 226.

The dust sensor included in the dust sensor circuit 44 is made of a reflective photointerrupter composing a light emitting element and a light receiving element to be optically coupled with the light emitting element. The light emitted by the light emitting element is reflected by dust in the air, and reaches the light receiving element. The light receiving element generates a voltage proportional to the quantity of light received. Therefore, by monitoring the output voltage of the light receiving element, it is possible to know the density of dust in the air.

The odor sensor included in the odor sensor circuit 45 is made of a metal oxide semiconductor. The metal oxide semiconductor changes its resistance by absorption of a gas component. Therefore, by monitoring the change in the resistance of the metal oxide semiconductor, it is possible to know the amount of gas component in the air, i.e., the level of "odor".

Note that both of the dust sensor and the odor sensor are placed somewhere inside the main body 5 where the air in the room passes through.

Next, the operation and function of the air purifier will be explained. When the operation of the air purifier starts, the fan motor driver circuit 47 receives a control signal from the microcomputer 33, and controls the fan motor 56 by PWM control to rotate at a predetermined ration speed, based on the control signal. With the rotation of the fan motor 56, the fan 57 rotates, and air inside the room is sucked through the air inlet 71 and the side-face air inlet 72. Relatively large dust in the sucked air is captured by the pre-filter 61, and subsequently a smelling component such as acetaldehyde, ammonia, and acetic acid is absorbed by the deodorizing filter 62. Further, minute dust in the air which has passed through the deodorizing filter 62 is captured by the dust collecting filter 63, and the resulting clean air containing no odor and dust moves toward the air passage 58.

A part of air which entered the air passage 58 enters the bypass passage 59 and is supplied to the ion generating electrode body 1. In the ion generating electrode body 1, an alternating voltage of about 1.8 kV is applied across the internal electrode 12 and the external electrode 13, and positive ions and negative ions are generated outside of the glass tube 11 that is a dielectric body.

At this time, if the relay 32 is in the on state, substantially equal amounts of positive ions and negative ions are generated as described above. This is the "first operation mode".

The positive ions and negative ions generated in substantially equal amounts by the "first operation mode" surround bacteria, and produce hydrogen peroxide $H_2O_2$ or hydroxyl group radical (—OH) as active species by chemical reaction, thereby removing/killing bacteria floating in the air in the room.

If the relay 32 is in the off state, a relatively large amount of negative ions and a relatively small amount of positive ions are generated (in the generation ratio of about 4:1 to 6:1) as described above. This is the "second operation mode".

When ion clusters with a high ratio of negative ions generated in the "second operation mode" are emitted from the ion outlet 82, they provide a relaxation effect on the people in the room.

The microcomputer 33 receives a signal from the key input circuit 109, and controls operation as follows.

When the air purifier is in a stopped state, the operation is started by pressing the "Operation On/Off" button 200 of the control unit 54 or the "Operation On/Off" button 230 of the remoter controller 41. When the "Operation On/Off" button 200 or 230 is pressed, the operation is started in an "automatic operation mode".

The "automatic operation mode" is an operation mode in which the rotation speed of the fan motor 56 is changed according to the amount of dust and odor in the air detected by the dust sensor circuit 44 and the odor sensor circuit 45. More specifically, one mode is selected from later described "silent operation mode", "low air volume operation mode", "medium air volume operation mode", and "high air volume operation mode". In the "automatic operation mode", the "Automatic Operation" lamp 211 is turned on. Moreover, the ion generator 10 starts operating. When the "Operation On/Off" button 200 or 230 is pressed during such automatic operation, the fan motor 56 is stopped, the operation of the ion generator 10 is also stopped, and the "Automatic Operation" lamp 211 is turned off.

When the air purifier is in operation, if the "Operation Switch" button 201 is pressed, each time the button 210 is pressed, the operation mode switches to "automatic operation mode"→"silent operation mode"→"low air volume operation mode"→"medium air volume operation mode"→"high air volume operation mode"→"rapid operation mode"→"cigarette operation mode"→"pollen operation mode"→"automatic operation mode". Accordingly, a lamp to be turned on also changes in the order of "Automatic Operation" lamp 211, "Silent Operation" lamp 212, "Mild Operation" lamp 213, "Normal Operation" lamp 214, "Strong Operation" lamp 215, "Rapid Operation" lamp 216, "Cigarette Operation" lamp 217, and "Pollen Operation" lamp 218. Note that, when the remote controller 41 is used to switch the operation modes, selection of the "automatic operation mode", "silent operation mode", "rapid operation mode", "cigarette operation mode", and "pollen operation mode" is made by the "Automatic Operation" button 235, "Silent Operation" button 236, "Rapid Operation" button 237, "Cigarette Operation" button 238, and "Pollen Operation" button 239, respectively, while selection of the "low air volume operation mode", "medium air volume operation mode", and "high air volume operation mode" is made by the "Manual Operation (Air Volume)" button 234.

In the "silent operation mode, the fan motor 56 is controlled so that the rotation speed thereof is 300 rpm. In this case, since the level of noise generated from the air purifier is low, this mode is suitable for use at night.

The fan motor 56 is controlled so that the rotation speed thereof is 550 rpm in the "low air volume operation mode", 750 rpm in the "middle air volume operation mode", and 950 rpm in the "high air volume operation mode", respectively.

In the "rapid operation mode", the fan motor 56 is controlled so that the rotation speed thereof is 1,100 rpm. In this case, since a larger amount of air passes through the filter 6, this mode is suitable for situations where the air needs to be cleaned quickly.

In the "cigarette operation mode", after performing operation in the "high air volume operation mode" for a certain time, the air purifier operates in the "automatic operation mode". First, the air purifier operates in the "high air volume" for a certain time to decrease the air pollution level in the room for a time, and then switches to automatic operation in which the rotation speed of the fan motor 56 is changed according to the dust and odor (cigarette smoke and odor in this case).

In the "pollen operation mode", after performing operation in the "high air volume operation mode" for a certain time, the air purifier operates by repeatedly switching between "low air volume operation mode" and "high air volume operation mode" at certain time intervals. Even when the amount of pollen is in such level as to cause people having pollen allergy to suffer, if the pollen is seen as dust floating in the air, its dust density is much smaller compared to cigarette smoke, and thus pollen is hard to be distinguished from floating dust of normal level. Therefore, the "high air volume operation" is repeated to increase the amount of air passing through the filter 6 and try to capture pollen as much as possible. If only the "high air volume operation" is performed continuously, the operation noise may offend peoples' ears, and therefore the "low air volume operation" is performed between the "high air volume operations".

When the "Off Timer" button 202 or 231 is pressed during operation, the operation of the air purifier can be stopped automatically after a set time. Each time the "Off Timer" button 202 or 231 is pressed, the set time changes to "1 hour"→"2 hours"→"4 hours"→"timer deactivated"→"1 hour". A lamp to be turned on also changes to the "1-hour" lamp 219→"2-hour" lamp 220→"4-hour" lamp 221→none→"1-hour" lamp 219. When the "Off Timer" button 231 of the remote controller 41 is pressed, electronic beeps corresponding to the set time are generated. It is therefore possible to know the set time for stopping the operation even from a place from where it is hard to see the lamps.

Although it is mentioned above that the ion generator 10 starts operating with the start of operation of the air purifier, it is also possible to actuate the ion generator 10 by the "Cluster On/Off" button 232 of the remote controller 41. When the "Cluster On/Off" button 232 is pressed while the ion generator 10 is not in operation, the SSR 35 is turned on, the ion generator 10 starts operating, and the cluster lamp is turned on. In other words, the view window 55 lights up. When the "Cluster On/Off" button 232 is pressed while the ion generator 10 is in operation, the SSR 35 is turned off, and the ion generator 10 stops operating. Since the control signal of the SSR 35 and the PWM control signal of the fan motor driver circuit 47 are mutually independent, it is possible to control the on/off state of the ion generator 10 irrespective of the on/off state of the fan motor 56.

Moreover, by pressing the "Cluster Switch" button 233 of the remote controller 41, the above-mentioned "first operation mode" and "second operation mode" are selected alternately.

Figure 12:
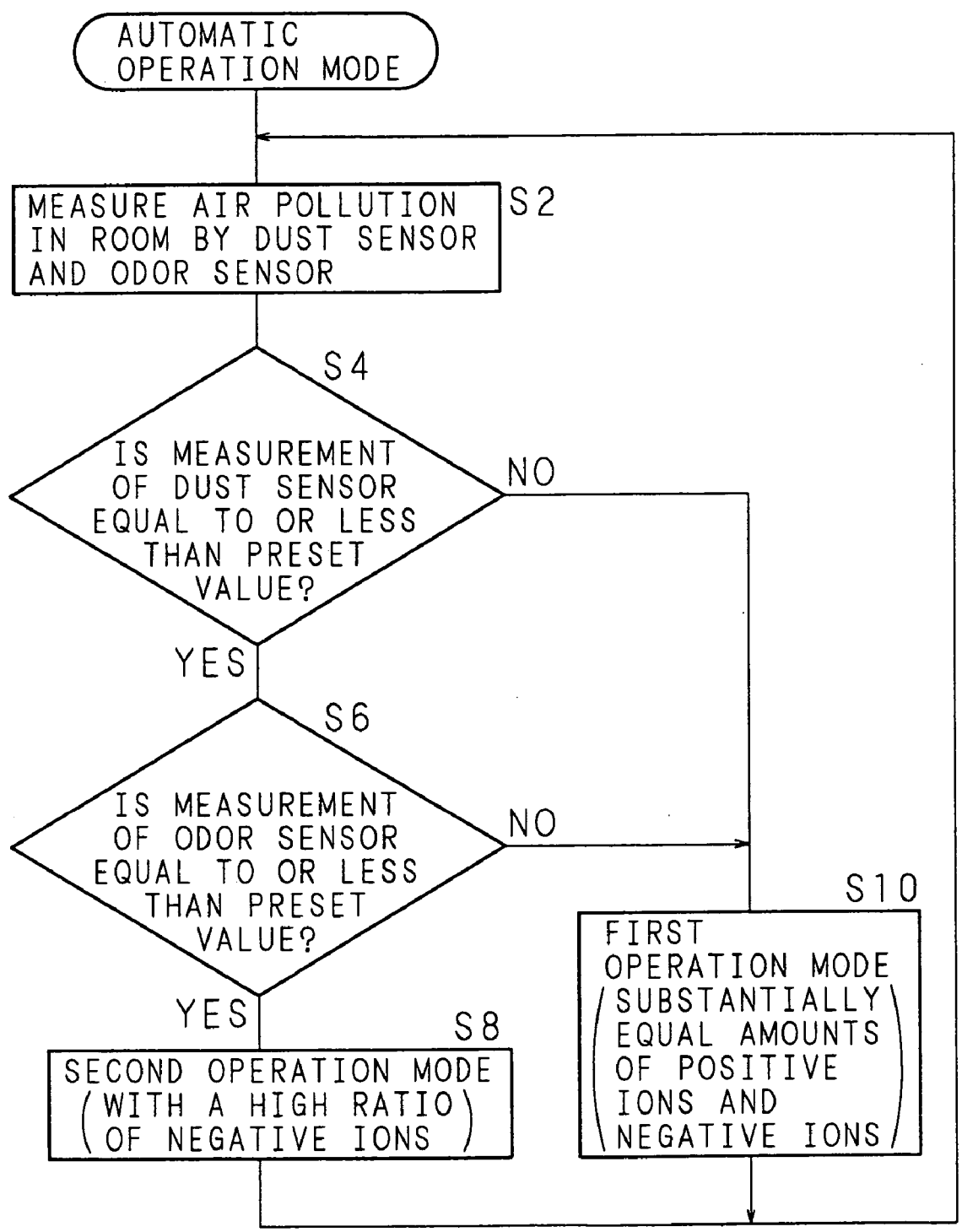
FIG. 12 is a flow chart showing the operation of the air purifier.

By the way, in the "automatic operation mode", the SSR 35 is in the on state, and the dust sensor and the odor sensor measure the air pollution level in the room (S2) as shown by the flow chart of FIG. 12. When the measurement of one of the sensors is greater than a preset value (S4), i.e., when the air is polluted, operation in the "first operation mode" is performed, i.e., operation of generating substantially equal amounts of positive ions and negative ions is performed (S10), according to an instruction of the microcomputer 33, aiming principally for air purification. When the measurements of both the sensors are equal to or less than the preset value (S6), it is judged that the air inside the room is clean, and operation in the "second operation mode" is performed, i.e., operation of generating a larger amount of negative ions and a smaller amount of positive ions is performed (S8), aiming principally for a relaxation effect rather than air purification. A mode in which operation is performed by automatically switching between the "first operation mode" and the "second operation mode" in the above-mentioned manner is a "third operation mode".

Figure 13:
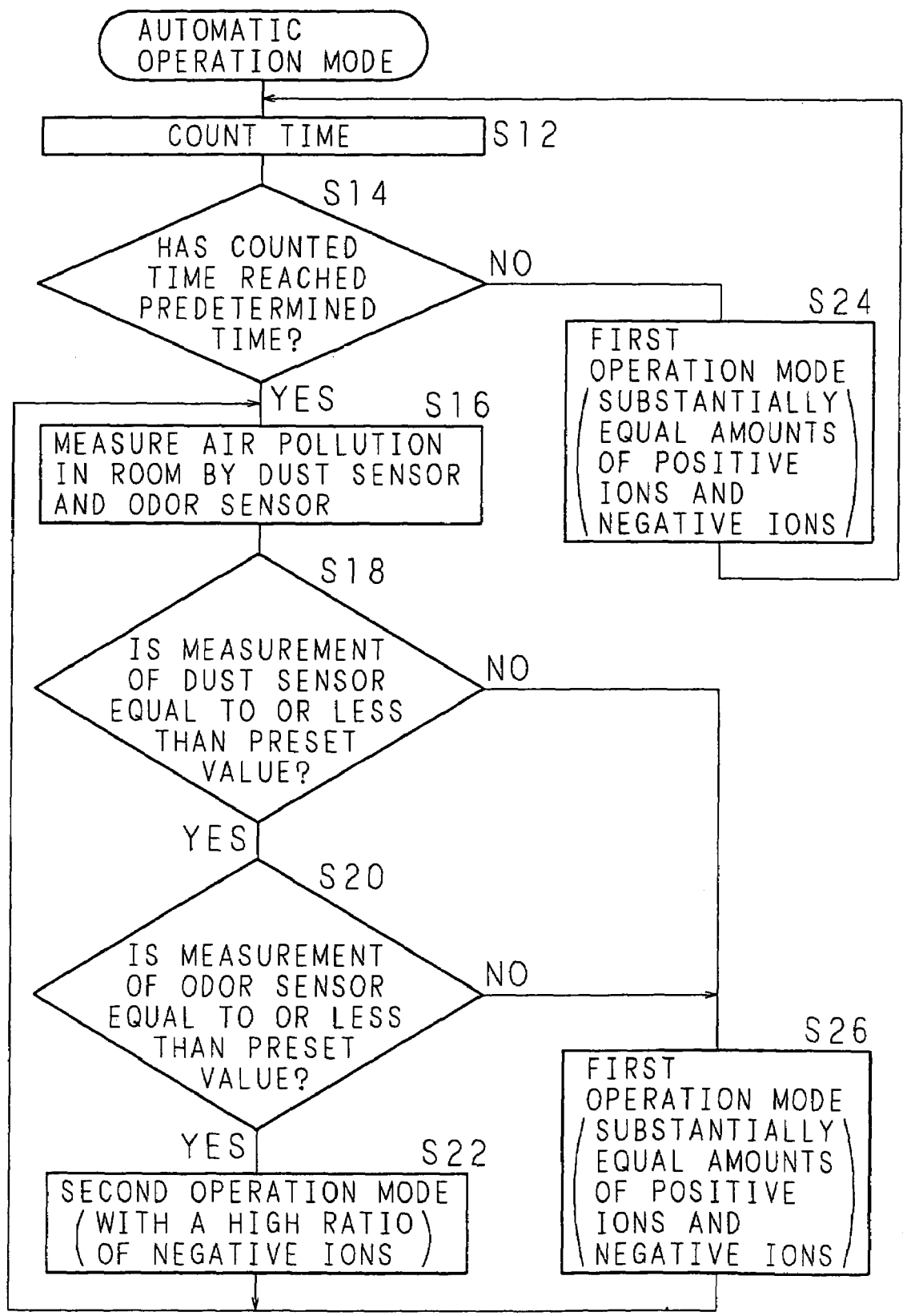
FIG. 13 is a flow chart showing the operation of the air purifier.

Besides, in the "automatic operation mode", the operation may also be performed as shown by the flow chart of FIG. 13.

When the "Automatic Operation" button 235 of the remote controller 41 is pressed, the microcomputer 33 starts the operation in the "automatic operation mode", and counts (measures) the time (S12).

At this time, the fan 57 is rotated by the fan motor 56, air is sucked into the air purifier, and an odor component and minute dust are removed from the sucked air by the filter 6. The air from which the dust and odor were removed by the filter 6 is discharged out of the air purifier by the fan 57.

In the ion generator 10, an alternating voltage is being applied after the start of operation of the air purifier, and the SSR 35 is in the on state in the "automatic operation mode".

The microcomputer 33 turns off the relay 32 until the counted time reaches a predetermined time (S14), and causes the ion generator 10 to perform the operation in the first operation mode to generate substantially equal amounts of positive ions and negative ions alternately (by a sinusoidal voltage) (S14).

After the counted time has reached the predetermined time (S14), the microcomputer 33 detects (measures) the air pollution condition in the room with the dust sensor circuit 44 and the odor sensor circuit 45 all the time (S16).

When both or one of the values detected by the sensor circuits (S16) are/is greater than the respective preset values (S18, 20), i.e., when the air in the room is dirty, the microcomputer 33 turns off the relay 32 and causes the ion generator 10 to perform the operation in the first operation mode to generate substantially equal amounts of positive ions and negative ions alternately (by a sinusoidal voltage) (S26).

On the other hand, when the values detected by the sensor circuits (S16) are both smaller than the respective preset values (S18, 20), i.e., when the air in the room is clean, the microcomputer 33 turns on the relay 32 with a control signal and causes the ion generator 10 to perform the operation in the second operation mode to generate ions in a ratio in which the amount of negative ions generated is higher than that of positive ions generated (S22).

Thus, when a predetermined time has not elapsed after the start of operation, and when the air in the room is polluted by both or either of dust and odor, the microcomputer 33 causes the ion generator 10 to operate in the first operation mode so as to generate substantially equal amounts of negative ions and positive ions and emit them into the room. Consequently, the floating bacteria is removed from the air in the room by the functions of the negative ions and positive ions.

According to the experiments performed by the present inventor et al., when the operation was performed in the "first operation mode", the removal ratio of floating bacteria was 86% after 2 hours from the start of the operation, 93% after 4 hours, and 99% after 20 hours.

Note that, while it is mentioned above that the cluster lamp in the view window 55 is composed of a plurality of light emitting diodes which emit light of different colors, it becomes easier to distinguish "Air Purification" and "Relaxation" from each other visually, if the indicator color in the "first operation mode" is set blue and the indicator color in the "second operation mode" is set green, for example.

The EEPROM circuit 112 writes the accumulated operation time of the motor 56 into the EEPROM. When the accumulated operation time reaches a predetermined value, the "Filter Replacement" lamp 222 is turned on to urge the user to replace the filter 6. After the filter replacement, the memory of the EEPROM is reset by pressing the filter reset button 225 with something having a sharp point.

While the above description explained embodiments in which the ion generator is incorporated into the air purifier, it is of course possible to incorporate the ion generator into other air conditioning apparatuses such as dehumidifiers, humidifiers, and air conditioners. In this case, in addition to each air conditioning apparatus's own function, the "Air Purification" function and "Relaxation" function of the ion generator of the present invention are exhibited. Besides, the present invention can be embodied by adding various changes to its details within the scope of the present invention.

INDUSTRIAL APPLICABILITY

According to the ion generator of the present invention, it is possible to generate substantially equal amounts of positive ions and negative ions or generate a relatively small amount of positive ions and a relatively large amount of negative ions, and to select a mode of ion generation according to a purpose in such a manner that substantially equal amounts of positive ions and negative ions are generated when the principal aim is to produce a bacteria removal/disinfection effect, and a larger amount of negative ions are generated compared to positive ions when a slight bacteria removal/disinfection effect is desired while aiming principally at producing a relaxation effect.

Moreover, according to the ion generator of the present invention, switching can be performed with a relatively simple circuit structure.

Furthermore, according to the ion generator of the present invention, the positioning of the diode and the switching means becomes easier, thereby reducing the manufacturing costs.

In addition, according to the ion generator of the present invention, it is possible to automatically maintain comfortable air quality in a room.

Besides, according to the ion generator of the present invention, it is possible to perform operation in an optimum operation mode according to the air pollution level.

Further, according to the ion generator of the present invention, it is possible to perform operation in such a health-oriented manner that, when the air pollution level is high, priority is given to bacteria removal/disinfection, and then, when the air pollution level is lowered, priority is shifted to a relaxation effect.

Moreover, according to the ion generator of the present invention, it is possible to know with a single glance whether positive ions having a bacteria removal/disinfection effect are emitted or negative ions having a relaxation effect are mainly emitted.

Furthermore, according to the ion generator of the present invention, it is possible to perform operation in an operation mode of generating substantially equal amounts of positive ions and negative ions, capable of producing a bacteria removal/disinfection effect, at the start of operation, at which time the air is considered dirty.

In addition, according to the ion generator of the present invention, it is possible to perform operation in an operation mode of generating substantially equal amounts of positive ions and negative ions, capable of producing a bacteria removal/disinfection effect, for a predetermined time from the start of operation at which time the air is considered dirty, and, after a lapse of the predetermined time, it is possible to switch between the operation mode of generating substantially equal amounts of negative ions and positive ions and an operation mode of generating a larger amount of negative ions, according to the air pollution level.

Besides, according to an air conditioning apparatus of the present invention, a bacteria removal/disinfection effect and a relaxation effect are produced in addition to an air conditioning effect inherent to the air conditioning apparatus, thereby making the indoor environment more comfortable.

The invention claimed is:

1. An ion generator comprising:
a first generator for generating positive ions and negative ions;
a second generator for generating a relatively small amount of positive ions and a relatively large amount of negative ions; and
a switch unit for selectively switching to either of the first generator and the second generator,
whereby either of the first generator and the second generator to which the switch unit switches is operated, and
wherein the first generator and the second generator comprise a dielectric body, a pair of electrodes facing each other with the dielectric body therebetween, and an applying unit for applying an alternating voltage across the pair of electrodes,
the applying unit applies an alternating voltage across the pair of electrodes to generate negative ions and positive ions,
and the switch unit includes a diode having an anode side connected to one of the pair of electrodes, which is not a voltage supply side electrode, and a cathode side to which a common fixed electric potential is applied, and a switch connected to both terminals of the diode.

2. The ion generator according to claim 1, wherein the diode and the switch are provided independently from the applying unit.

3. An ion generator comprising:
a first generator for generating positive ions and negative ions;
a second generator for generating a relatively small amount of positive ions and a relatively large amount of negative ions;
a switch unit for selectively switching to either of the first generator and the second generator; and
one of a timer and a detector for detecting an external environment,
whereby either of the first generator and the second generator to which the switch unit switches is operated, and
wherein the switch unit switches based on one of a time measured by the timer and a value detected by the detector.

4. The ion generator according to claim 3, wherein the detector is a sensor for detecting an air pollution level.

5. The ion generator according to claim 4, further comprising a timer,
wherein the switch unit switches to the first generator for a predetermined time which is measured from start of operation by the timer, and, after the timer has measured the predetermined time, the switch unit switches based on a pollution level detected by the sensor.

6. The ion generator according to claim 4, further comprising a setting unit for externally setting the air pollution level,
wherein the switch unit switches to the first generator when the value detected by the sensor is not less than a value set by the setting unit, and switches to the second generator when the detected value is less than the set value.

7. The ion generator according to claim 6, further comprising a timer,
wherein the switch unit switches to the first generator for a predetermined time which is measured from start of operation by the timer, and, after the timer has measured the predetermined time, the switch unit switches based on a pollution level detected by the sensor.

8. An ion generator comprising:
a first generator for generating positive ions and negative ions;
a second generator for generating a relatively small amount of positive ions and a relatively large amount of negative ions;
a switch unit for selectively switching to either of the first generator and the second generator; and
an indicator for indicating an operational state,
whereby either of the first generator and the second generator to which the switch unit switches is operated, and
wherein, when one of the first generator and the second generator is in operation, the indicator indicates operational state thereof by a corresponding color.

9. An ion generator comprising:
a first generator for generating positive ions and negative ions;
a second generator for generating a relatively small amount of positive ions and a relatively large amount of negative ions;
a switch unit for selectively switching to either of the first generator and the second generator; and
a timer,
whereby either of the first generator and the second generator to which the switch unit switches is operated, and
wherein the switch unit switches to the first generator for a predetermined time which is measured from start of operation by the timer.

10. An air conditioning apparatus comprising:
a changing unit for changing air conditions; and
an ion generator, the ion generator comprising:
a first generator for generating substantially equal amounts of positive ions and negative ions;

a second generator for generating a relatively small amount of positive ions and a relatively large amount of negative ions; and a switch unit for selectively switching to either of the first generator and the second generator, whereby negative ions and positive ions generated by the ion generator are dispersed into the air changed by the changing unit, and either of the first generator and the second generator to which the switch unit switches is operated, wherein the first generator and the second generator comprise a dielectric body, a pair of electrodes facing each other with the dielectric body therebetween, and an applying unit for applying an alternating voltage across the pair of electrodes, the applying unit applies an alternating voltage across the pair of electrodes to generate negative ions and positive ions, and the switch unit includes a diode having an anode side connected to one of the pair of electrodes, which is not a voltage supply side electrode, and a cathode side to which a common fixed electric potential is applied, and a switch connected to both terminals of the diode.

11. The air conditioning apparatus according to claim 10, wherein the diode and the switch are provided independently from the applying unit.

12. An air conditioning apparatus comprising:
a changing unit for changing air conditions; and
an ion generator, the ion generator comprising:
a first generator for generating substantially equal amounts of positive ions and negative ions;
a second generator for generating a relatively small amount of positive ions; and a relatively large amount of negative ions;
a switch unit for selectively switching to either of the first generator and the second generator, whereby negative ions and positive ions generated by the ion generator are dispersed into the air changed by the changing unit, and either of the first generator and the second generator to which the switch unit switches is operated; and
one of a timer and a detector for detecting an external environment,
wherein the switch unit switches based on one of a time measured by the timer and a value detected by the detector.

13. The air conditioning apparatus according to claim 12, wherein the detector is a sensor for detecting an air pollution level.

14. The air conditioning apparatus according to claim 13, the ion generator further comprising a timer,
wherein the switch unit switches to the first generator for a predetermined time which is measured from start of operation by the timer, and, after the timer has measured the predetermined time, the switch unit switches based on a pollution level detected by the sensor.

15. The air conditioning apparatus according to claim 13, the ion generator further comprising a setting unit for externally setting the air pollution level,
wherein the switch unit switches to the first generator when the value detected by the sensor is not less than a value set by the setting unit, and switches to the second generator when the detected value is less than the set value.

16. The air conditioning apparatus according to claim 15, the ion generator further comprising a timer,
wherein the switch unit switches to the first generator for a predetermined time which is measured from start of operation by the timer, and, after the timer has measured the predetermined time, the switch unit switches based on a pollution level detected by the sensor.

17. An air conditioning apparatus comprising:
a changing unit for changing air conditions; and
an ion generator, the ion generator comprising:
a first generator for generating substantially equal amounts of positive ions and negative ions;
a second generator for generating a relatively small amount of positive ions; and a relatively large amount of negative ions;
a switch unit for selectively switching to either of the first generator and the second generator, whereby negative ions and positive ions generated by the ion generator are dispersed into the air changed by the changing unit, and either of the first generator and the second generator to which the switch unit switches is operated; and
an indicator for indicating an operational state,
wherein, when one of the first generator and the second generator is in operation, the indicator indicates operational state thereof by a corresponding color.

18. An air conditioning apparatus comprising:
a changing unit for changing air conditions; and
an ion generator, the ion generator comprising:
a first generator for generating substantially equal amounts of positive ions and negative ions;
a second generator for generating a relatively small amount of positive ions; and a relatively large amount of negative ions;
a switch unit for selectively switching to either of the first generator and the second generator, whereby negative ions and positive ions generated by the ion generator are dispersed into the air changed by the changing unit, and either of the first generator and the second generator to which the switch unit switches is operated; and
a timer,
wherein the switch unit switches to the first generator for a predetermined time which is measured from start of operation by the timer.

* * * * *

UNITED STATES PATENT AND TRADEMARK OFFICE
CERTIFICATE OF CORRECTION

PATENT NO.         : 7,120,006 B2
APPLICATION NO.    : 10/475121
DATED              : October 10, 2006
INVENTOR(S)        : Yoshinori Sekoguchi et al.

It is certified that error appears in the above-identified patent and that said Letters Patent is hereby corrected as shown below:

On the Title page, item (56) References Cited, FOREIGN PATENT DOCUMENTS, please add the following references:

| | | | |
|---|---|---|---|
| JP | 2001-70830 | A | 03/2001 |
| JP | 8-255669 | A | 10/1996 |
| JP | 2002-95731 | A | 04/2002 |
| JP | 7-108147 | A | 04/1995 |
| JP | 2001-42598 | A | 02/2001 |
| JP | 11-251035 | A | 09/1999 |
| JP | 10-12395 | A | 01/1998 |
| JP | 2002-305070 | A | 10/2002 |
| JP | 2002-25748 | A | 01/2002 |
| JP | 2001-179131 | A | 07/2001 |
| JP | 2000-167435 | A | 06/2000 |
| JP | 2000-185099 | A | 07/2000 |
| JP | 08-217412 | A | 08/1996 |
| JP | 2000-058290 | A | 02/2000 |

Signed and Sealed this

Twentieth Day of February, 2007

JON W. DUDAS
*Director of the United States Patent and Trademark Office*